United States Patent [19]
Strickman et al.

[11] 4,061,144
[45] Dec. 6, 1977

[54] DISPOSABLE SYRINGE

[76] Inventors: Robert L. Strickman, 729 Handwerg Drive, River Vale, N.J. 07675; Melvyn B. Strickman, Academy St., Shiloh, N.J. 08353

[21] Appl. No.: 684,906

[22] Filed: May 10, 1976

[51] Int. Cl.² ............................................... A61M 7/02
[52] U.S. Cl. ..................................... 128/227; 128/251
[58] Field of Search ................. 128/251, 227, DIG. 24

[56] References Cited
U.S. PATENT DOCUMENTS 2,917,047  12/1959  Milton ................................... 128/227

Primary Examiner—John D. Yasko
Attorney, Agent, or Firm—Charles E. Baxley

[57] ABSTRACT

This disclosure teaches a disposable syringe, preferably made of biodegradable paper, and adapted for vaginal douching. A tubular nozzle is provided with an axial passage and has a first end insertable into a woman's vagina as well as a second end sealed to a flexible bag that encloses a reservoir. At least one spray opening is formed in the first end of the nozzle and it communicates in flow series with the reservoir via the axial passage. A membrane in the bag is adapted to contain a douche powder therein. Means are provided, for example a pull string, to tear the membrane for mixing the douche powder with water in the reservoir.

2 Claims, 4 Drawing Figures

U.S. Patent     Dec. 6, 1977     4,061,144
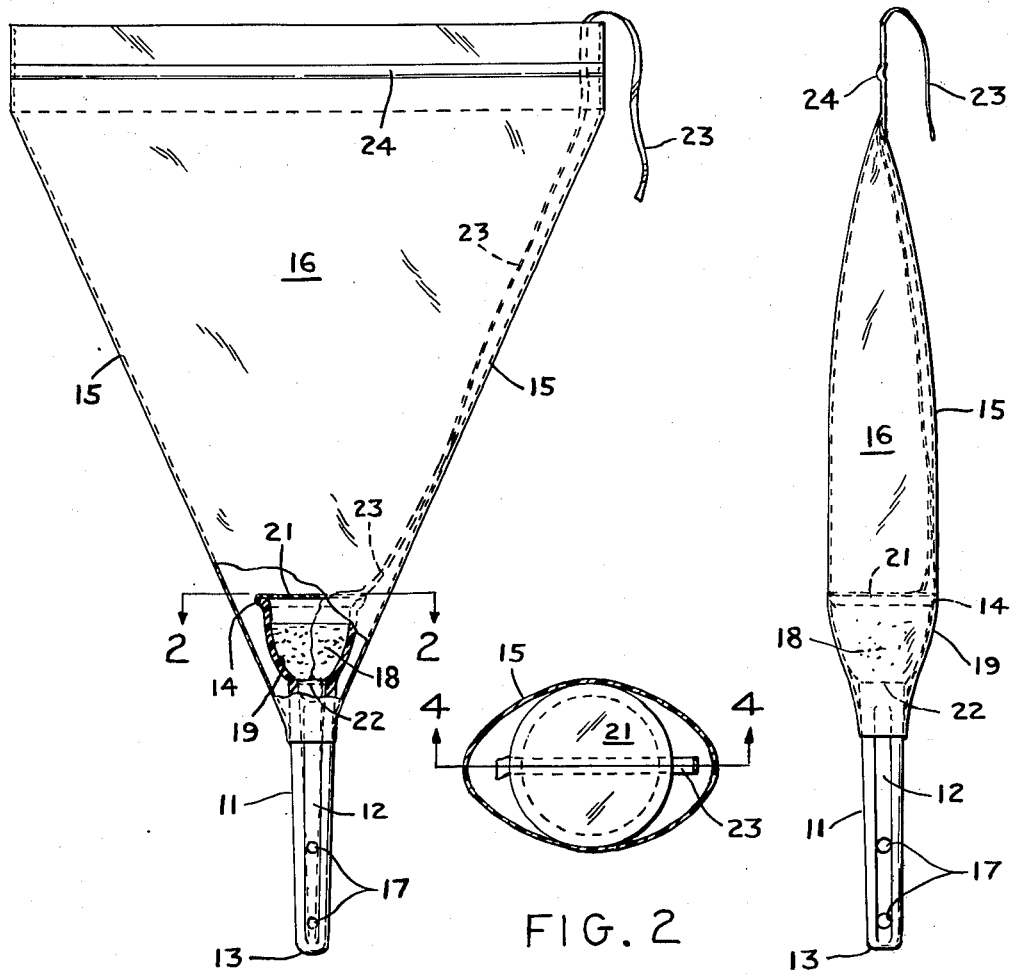
FIG. 1
FIG. 2
FIG. 3
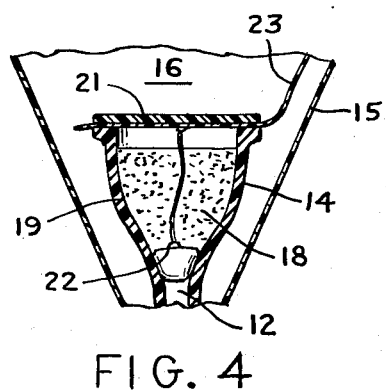
FIG. 4

DISPOSABLE SYRINGE

BACKGROUND OF INVENTION

This invention relates to an improved device for cleansing a woman's vaginal tract.

Douche bags have become a matter of necessity, according to modern standards of feminine hygiene, to such an extent that they generally are considered a necessary implement even during travel. Toward this objective manufacturers strive to make the bags in such a manner that they may be stored easily in a minimum of space. Despite such facilitation, it happens frequently that a woman finds herself embarrassed for need of one of these items when away from home. In such a case, it is not a welcome solution to purchase an extra bag of the type capable of long term use. According to the present invention, there is provided a douche syringe which can be sold at less cost and therefore may be discarded after a single use. Also being composed largely of thin biodegradable paper, the douche syringe may be folded into a small, compact, inconspicuous bundle, so that one or several packages may be included in a traveling bag, or even a handbag without seriously compromising storage capacity available for other articles. Being made of biodegradable paper, these douche syringes after being used may be disposed of in any trash depository such as a waste basket or they may be flushed down a toilet.

STATEMENT OF INVENTION

A disposable vaginal syringe according to this invention overcomes disadvantages and shortcomings of prior art devices of its type in a useful, novel, unobvious and particularly facile way. A tubular nozzle is provided with an axial passage and has a first end insertable into a woman's vagina as well as a second end sealed to a flexible bag that encloses a reservoir. At least one spray opening is formed in the first end of the nozzle and it communicates in flow series with the reservoir via the axial passage. A membrane in the bag is adapted to contain a douche powder therein. A tearing means (for example a pull string) is provided to tear the membrane for mixing of the douche powder with water in the reservoir.

Accordingly it is an object of this invention to provide a douche syringe which is low in cost, so as to be disposable after a single use.

A further object of this invention is to provide a douche syringe which may be consolidated into a comparitively small volume for carrying purposes, and ease of merchandising.

A still further object of this invention is to provide a douche syringe which contains a desired quantity of douche powder in a convenient rupturable compartment.

It is still a further object of this invention to provide a douche syringe which otherwise is well suited to its intended function.

BRIEF DESCRIPTION OF DRAWING

The foregoing objects, features and advantages will appear more fully from an accompanying drawing, viewed in conjunction with a detailed description which follows and further viewed in conjunction with claims which also follow. In the drawing like numerals designate like parts throughout and:

FIG. 1 is a partly broken side view of a douche syringe according to this invention.
FIG. 2 is a sectional view taken along line 2—2 of FIG. 1.
FIG. 3 is an end view of the douche.
FIG. 4 is a broken sectional view taken along line 4—4 of FIG. 2.

DETAILED DESCRIPTION OF PREFERRED EMBODIMENT

As shown in the drawing the vaginal syringe of this invention includes a tubular nozzle 11 which has an axial passage 12. The nozzle 11 has a first end 13 which is insertable into a body cavity (usually a woman's vagina) and a second end 14 connected in sealed engagement with a flexible bag 15 which encloses a reservoir 16. The axial passage 12 communicates in flow series with the reservoir 16 and with spray openings 17 in the first end 13 of the nozzle 11.

Douche powder 18 is stored in an enlarged section 19 of the second end 14 of the nozzle 11 and is contained by inner membrane 21 and outer membrane 22 both of which are connected to a pull string 23 which penetrates out of the reservoir 16 through a tongue and groove seam 24. The reservoir 16 is filled with water while the tongue and groove seam 24 is open. On pulling the pull string 23 the membranes 21, 22 are ruptured releasing the douche powder 18 to the water in the reservoir 16.

It will be apparent to those skilled in design manufacture and use of douche syringes that wide deviations may be made from the foregoing preferred embodiment without departing from a main theme of invention set forth in claims which follow.

We claim:
1. A disposable compact vaginal syringe comprising in combination the following:
   a tubular nozzle having an axial passage therethrough,
   the nozzle having a first end insertable into a vaginal cavity of a user and a second end connected in sealed engagement with a foldable flexible bag which is holdable in the user's hand and which encloses a reservoir,
   the nozzle provided with a compartment in the second end thereof to store douche powder therein,
   the axial passage communicating in flow series between the reservoir and at least one spray opening in the first end of the nozzle,
   the bag provided with an opening whereby the reservoir is fillable with water,
   the bag having a tongue in groove seal to close the opening,
   at least one membrane enclosing the douche powder in the compartment,
   a pull member connected to the membrane and extending out of the bag via the opening for tearing the membrane to release the douche powder into the water in the reservoir, the reservoir squeezable manually by the user to inject the water with the douche powder dissolved therein into the user's vaginal cavity for cleansing thereof.
2. The disposable compact vaginal syringe as set forth in claim 1, wherein:
   the membrane includes an inward membrane portion and an outer membrane portion organized to enclose the douche powder therebetween in the compartment,
   both the inward membrane portion and the outer membrane portion connected to the pull member.

* * * * *